United States Patent [19]
Gryaznov

[11] Patent Number: 5,571,677
[45] Date of Patent: Nov. 5, 1996

[54] CONVERGENT SYNTHESIS OF BRANCHED AND MULTIPLY CONNECTED MACROMOMOLECULAR STRUCTURES

[75] Inventor: Sergei M. Gryaznov, San Mateo, Calif.

[73] Assignee: LYNX Therapeutics, Inc., Hayward, Calif.

[21] Appl. No.: 455,627

[22] Filed: May 31, 1995

Related U.S. Application Data

[63] Continuation of Ser. No. 87,386, Jul. 2, 1993.
[51] Int. Cl.$^6$ .............................. C12Q 1/68; C12Q 1/70; C12P 19/34; C07H 21/04
[52] U.S. Cl. ................. 435/6; 435/5; 435/91.1; 435/91.2; 435/7.1; 536/24.3; 536/24.31; 536/24.32; 536/24.33
[58] Field of Search .................................. 435/6, 5, 91.1, 435/91.2, 7.1–7.9, 26.6; 536/24.3–24.33

[56] References Cited

U.S. PATENT DOCUMENTS

| | | | |
|---|---|---|---|
| 4,775,619 | 10/1988 | Urdea | 435/6 |
| 5,245,022 | 9/1993 | Weis et al. | 536/24.5 |
| 5,256,775 | 10/1993 | Froehler | 536/25.6 |
| 5,473,060 | 12/1995 | Gryaznov et al. | 536/24.3 |
| 5,476,930 | 12/1995 | Letsinger | 536/25.3 |

OTHER PUBLICATIONS

S. Agrawal et al., "Oligodeoxynucleoside phosphoramidates and phosphorothioates as inhibitors of human immunodeficiency virus", *Proc. Natl. Acad. Sci. USA*, vol. 85, pp. 7079–7083, 1988.

C. Chang et al., "Improved methods for the synthesis of branched DNA (bDNA) for use as amplification multimers in bioassays", *Nucleosides & Nucleotides*, vol. 10(1–3), pp. 389–392, 1991.

J. M. Dagle et al., "Physical properties of oligonucleotides containing phosphoramidate–modified internucleoside linkages", *Nucleic Acids Research*, vol. 19 (8), pp. 1805–1810, 1991.

N. Dolinnaya et al., "Construction of branched DNA (bDNA) molecules by chemical ligation", *Bioorganic & Medicinal Chemistry Letters*, vol. 4 (8), pp. 1011–1018, 1994.

J. C. Francois et al., "Periodic cleavage of poly(dA) by oligothymidylates covalently linked to the 1,10-phenanthroline–copper–complex", *Biochemistry*, vol. 27, pp. 2272–2276, 1988.

M. A. Grachev et al., "A route to RNA with an alkylating group at the 5'-triphosphate residue", *Nucleic Acids Research*, vol. 8(15), pp. 3413–3426, 1980.

R. R. Hodges et al., "'Post–assay' covalent labeling of phosphorothioate–containing nucleic acids with multiple flourescent markers", *Biochemistry*, vol. 28, pp. 261–267, 1989.

T. Horn et al., "Solid supported chemical 5'–phosphorylation of oligodeoxy–ribonucleotides that can be monitored by trityl cation release: application to gene synthesis", *Nucleosides & Nucleotides*, vol. 6 (1–2), pp. 335–340, 1987.

T. Horn et al., "The synthesis of branched oligonucleotides as signal amplification multimers for use in nucleic acid assay", *Nucleosides & Nucleotides*, vol. 8 (5–6), pp. 875–877, 1989.

T. Le Doan et al., "Sequence–specific recognition, photo–crosslinking and cleavage of the DNA double helix by an oligo–[α]–thymidylate covalently linked to an azidoproflavine derivative", *Nucleic Acids Research*, vol. 15(19), pp. 7749–7760, 1987.

J. F. Milligan et al., "Current concepts in antisense drug design", *Journal of Medicinal Chemistry*, vol. 36(14), pp. 1923–1937, 1993.

S. I. Oshavski, "Enzymatic transfer of ATPγS thiophosphate onto the 5'hydroxyl of an oligonucleotice as a route to reactive oligonucleotide derivates", *FEBS Letters*, vol. 143(1), pp. 119–123, 1982.

D. Praseuth et al., "Sequence–specific binding and photo–crosslinking of α and β oligodeoxynucleotides to the major grove of DNA via triple–helix formation", *Proc. Natl. Acad. Sci. USA*, vol. 85, pp. 1349–1353, 1988.

Horn et al, Nucleic Acids Research 17: 6959–6967.

Goodchild et al., Bioconj. Chem. 1: 165–187.

Fidanza et al. J. Am Chem Society 111: 9117–9119.

*Primary Examiner*—Stephanie W. Zitomer
*Assistant Examiner*—Dianne Rees
*Attorney, Agent, or Firm*—Cooley Godward Castro Huddleson & Tatum

[57] ABSTRACT

The invention provides methods and compositons for convergent synthesis of branched polymers useful as molecular probes. The invention also includes several novel branched polymeric structures particularly useful for detecting target polynucleotides. Branched polymers of the invention comprise at least two branches: at least one branch is a target binding moiety capable of specifically binding to a target molecule of interest and one or more branches are signal generation moities capable of directly or indirectly generating a detectable signal. In accordance with the method of the invention branched polymers are assembled from components having phosphorothioate groups and/or haloacyl- or haloalkylamino groups. The phosphorothioate and haloacyl- or haloalkylamino groups react rapidly and efficiently when brought into contact to form thiophosphorylacyl- or thiophosphorylalkylamino bridges which.complete the assembly of a branched polymer. The method of the invention permits thorough purification and isolation of the components prior to final assembly. Incomplete branched polymers are readily separated from the desired product by standard means. The method of the invention permits the synthesis of several novel branched polymer configurations.

20 Claims, 2 Drawing Sheets

CONVERGENT SYNTHESIS OF BRANCHED AND MULTIPLY CONNECTED MACROMOMOLECULAR STRUCTURES

CROSS REFERENCE TO RELATED APPLICATIONS

This application is a continuation of U.S. application Ser. No. 08/087,386, filed Jul. 2, 1993.

The invention relates generally to polymer synthesis, and more particularly, to the synthesis of branched polymers and multiply connected macromolecular structures, such as macrocycles.

BACKGROUND

Polynucleotide detection and analysis is becoming increasingly important in many research, medical, and industrial fields, e.g. Caskey, Science 236: 1223–1228 (1987); Landegren et al, Science, 242:229–237 (1988); and Arnheim et al, Ann. Rev. Biochem., 61: 131–156 (1992). Several techniques have been developed which exploit the specific hybridization of a probe nucleic acid to a complementary target nucleic acid for detection of the target. Generally, the most powerful of such techniques involve some form of target sequence and/or signal amplification, e.g. polymerase chain reaction, Arnheim et al (cited above); ligation-based amplification, e.g. Barany, PCR Methods and Applications 1: 5–16 (1991); strand-displacement amplification, Walker et al, Proc. Natl. Acad. Sci., 89:392–396 (1992); branched probe signal amplification, Wang et al, U.S. Pat. No. 4,925,785, Urdea et al, U.S. Pat. No. 5,124, 246, Hudson et al, J. Am. Chem. Soc., 115:2119–2124 (1993); and the like.

In regard to the latter catagory of techniques, synthesis of the branched probe structures by current methods is typically difficult, results in low yields, and provides only limited and indirect means for monitoring yield and product quality during and after synthesis. Presently, most branched polymer approaches to polynucleotide detection do not lend themselves to the production of practical commercial assays.

SUMMARY OF THE INVENTION

The invention provides methods and compositions relating to the production and use of branched polymers, and other branched and multiply connected macromolecular structures, such as macrocycles. Preferably, branched polymers and multiply connected macromolecular structures of the invention comprise at least two branches and/or macrocycles: at least one branch or macrocycle is a target binding moiety capable of specifically binding to a target molecule of interest and one or more branches or macrocycles are signal generation moities capable of directly or indirectly generating a detectable signal. Preferably, the branched polymers and macrocycles of the invention comprise at least one oligonucleotide moiety as a target binding moiety. In accordance with the method of the invention branched polymers and other macromolecular structures are assembled from components having phosphorothioate or phosphorodithioate groups and having haloacyl- or haloalkylamino groups. The phosphorothioate or phosphorodithioate groups react rapidly and efficiently with haloacyl- or haloalkylamino groups when brought into contact to form thio- or dithiophosphorylacyl- or thio- or dithiophosphorylalkylamino bridges which complete the assembly of the desired structure. The method of the invention permits thorough purification and isolation of the components prior to the final assembly step. Incomplete branched polymers and/or other incomplete structures are readily separated from the desired product by standard means. An important aspect of the invention is that the thio- or dithiophosphorylacyl- or thio- or dithiophosphorylalkylamino bridges are readily and selectively cleaved by oxidation, which allows for convenient post synthesis confirmation of structure. The method of the invention further permits the synthesis of several novel branched polymer configurations.

DEFINITIONS

Figure 1A:
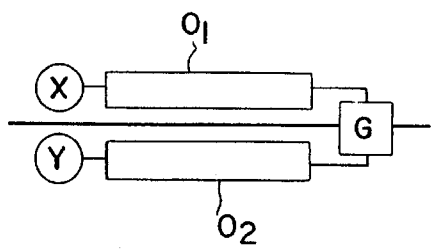
FIGS. 1a and 1b diagrammatically illustrate embodiments of oligonucleotide clamps FIG. 2 diagrammatically illustrates the structure of a doubly connected, or loop-type, branched polymer having four branches for attaching signal generating moieties.

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type base pairing, Hoogsteen type base pairing, or the like. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "ATGCCTG," it will be understood that the nucleotides are in 5'–>3' order from left to right and that "A" denotes deoxyadenosine, "C" denotes deoxycytidine, "G" denotes deoxyguanosine, and "T" denotes thymidine, unless otherwise noted.

Phosphorus linkages between nucleosidic monomers include phosphodiester bonds and analogs of phosphodiester bonds, such as phosphorothioate, phosphorodithioate, phosphoroselenoate, phosphorodiselenoate, phosphoroanilothioate, phosphoranilidate, and the like.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992) and analogs thereto, including synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, to provide reactive functionalities for branch points, attachment of labeling moieties, and the like.

"Stable" in reference to the formation of a covalent linkage and/or non-covalent complex between binding moieties means that melting temperature of the oligonucleotide clamp incorporating the given pair(s) of binding moieties and its target polynucleotide is increased by at least twenty-five percent over the melting temperature of oligonucleotide moieties of the clamp alone, wherein melting temperature is measured by standard techniques, e.g. half maximum of 260 nm absorbance v. temperature as described more fully below. Preferably, stable means that melting temperature of the oligonucleotide clamp incorporating the given pair(s) of binding moieties and its target polynucleotide is increased by at least fifty percent over the melting temperature of oligonucleotide moieties of the clamp alone.

"Stable" in reference to the formation of a complex between a target molecule and a branched or multiply connected macromolecular structure of the invention means that the dissociation rate of the target molecule and the branched or multiply connected macromolecular structure is sufficiently low as to permit the generation of a detectable signal. Preferably, the dissociation constant of the complex is at least $10^{-7}$M. More preferably, the dissociation constant of the complex is between about $10^{-8}$M to about $10^{-11}$M.

"Linkage" in reference to the reaction of binding moieties includes both covalent linkages and non-covalent complexes.

DETAILED DESCRIPTION OF THE INVENTION

The invention relates to methods and compositons for convergent synthesis of branched polymers and other branched and multiply connected macromolecular structures. The invention also includes several novel branched polymeric structures particularly useful for detecting target polynucleotides. Preferably, the branched polymers and branched and multiply connected macromolecular structures of the invention include a plurality of polymeric units that comprise signal generation moieties and at least one oligonucleotide moiety which serves as a target binding moiety. In one aspect such target binding moiety is an oligonucleotide clamp, as described more fully below.

Generally, branched polymers and branched and multiply connected macromolecular structures of the invention are assembled from a plurality of components which are separately synthesized and purified prior to assembly. Such components themselves may comprise branched, linear, or macrocyclic polymers, or combinations of the three, and may be the product of a prior assembly and isolation of. components. Usually, the components are constructed from linear polymeric units which may form the branches of the branched polymers or may be self-ligated to form loops or macrocycles. Branched polymers of the invention include comb-type branched polymers, which comprise a linear polymeric unit with one or more branch points located at interior monomers and/or linkage moieties. Branched polymers of the invention also include fork-type branched polymers, which comprise a linear polymeric unit with one or two branch points located at terminal monomers and/or linkage moieties. Branched and multiply connected macromolecular structures of the invention include macrocycles, e.g. wherein two linear polymeric units are doubly connected to form a covalently closed circular polymefic structure; macrocycles with branches, e.g. as disclosed in the examples below; multiply connected macrocycles, e.g. as with a macrocycle with a single branch whose ends connect to the macrocycle in two different locations, and like structures.

The branched polymers and other branched and multiply connected macromolecular structures of the invention have a variety of uses, particularly as molecular probes. The compounds of the invention are further useful as moieties for changing the electrophoretic mobility of polymefic compounds having a constant charge-to-mass ratios, such as polynucleotides, e.g. Noolandi, Electrophoresis, 13:394–395 (1992); Van Alstine, U.S. Pat. No. 5,108,568; Livak et al, Nucleic Acids Research, 20:4831–4837 (1992); and the like.

Polymeric Units

Preferably, the linear polymeric units of the invention have the form:

wherein L is a linker moiety and M is a monomer that may be selected from a wide range of chemical structures to provide a range of functions from serving as an inert non-sterically hindering spacer moiety to providing a reactive functionality which can serve as a branching point to attach other components, a site for attaching labels; a site for attaching oligonucleotides or other binding polymers for hybridizing or binding to amplifier strands or structures, e.g. as described by Urdea et al, U.S. Pat. No. 5,124,246 or Wang et al, U.S. Pat. No. 4,925,785; a site for attaching "hooks", e.g. as described in Whiteley et al, U.S. Pat. No. 4,883,750; or as a site for attaching other groups for affecting solubility, promotion of duplex and/or triplex formation, such as intercalators, alkylating agents, and the like. The following references disclose several phosphoramidite and/or hydrogen phosphonate monomers suitable for use in the present invention and provide guidance for their synthesis and inclusion into oligonucleotides: Newton et al, Nucleic Acids Research, 21:1155–1162 (1993); Griffin et al, J. Am. Chem. Soc., 114:7976–7982 (1992); Jaschke et al, Tetrahedron Letters, 34:301–304 (1992); Ma et al, International application PCT/CA92/00423; Zon et al, International application PCT/US90/06630; Durand et al, Nucleic Acids Research, 18:6353–6359 (1990); Salunkhe et al, J. Am. Chem. Soc., 114:8768–8772 (1992); Urdea et al, U.S. Pat. No. 5,093,232; Ruth, U.S. Pat. No. 4,948,882; Cruickshank, U.S. Pat. No. 5,091,519; Haralambidis et al, Nucleic Acids Research, 15:4857–4876 (1987); and the like. More particularly, M is a straight chain, cyclic, or branched organic molecular structure containing from 1 to 20 carbon atoms and from 0 to 10 heteroatoms selected from the group consisting of oxygen, nitrogen, and sulfur. Preferably, M is alkyl, alkoxy, alkenyl, or aryl containing from 1 to 16 carbon atoms; heterocyclic having from 3 to 8 carbon atoms and from 1 to 3 heteroatoms selected from the group consisting of oxygen, nitrogen, and sulfur; glycosyl; or nucleosidyl. More preferably, M is alkyl, alkoxy, alkenyl, or aryl containing from 1 to 8 carbon atoms; glycosyl; or nucleosidyl.

Preferably, L is a phosphorus(V) linking group which may be phosphodiester, phosphotriester, methyl or ethyl phosphonate, phosphorothioate, phosphorodithioate, phosphoramidate, or the like. Generally, linkages derived from pho sphoramidite or hydrogen phosphonate precursors are preferred so that the linear polymeric units of the invention can be conveniently synthesized with commercial automated DNA synthesizers, e.g. Applied Biosystems, Inc. (Foster City, Calif.) model 394, or the like.

n may vary significantly depending on the nature of M and L. Usually, n varies from about 3 to about 100. When M is a nucleoside or analog thereof or a nucleoside-sized monomer and L is a phosphorus(V) linkage, then n varies from about 12 to about 100. Preferably, when M is a nucleoside or analog thereof or a nucleoside-sized monomer and L is a phosphorus(V) linkage, then n varies from about 12 to about 40.

In accordance with the invention, at least one component of a branched polymer is an oligonucleotide that serves as target binding moiety. Such oligonucleotide is selected to bind specifically and stably with a desired target molecule. Usually, the desired target molecule will be a protein or a portion, or epitope, thereof or a polynucleotide. The binding specificity may be achieved by base-specific binding in the case of polynucleotides or it may be achieved by different mechanisms, such as with aptamer binding to general molecular structures, which may include carbohydrates, proteins, and other structures, as well as polynucleotides. In the latter case the sequence of the oligonucleotide moiety may be selected as taught by Ellington and Szostak, Nature, 346:818–822 (1990); Toole et al, International application PCT/US92/01383; and the like. Preferably, the affinity of the target binding moiety for its target, as measured by dissociation constant, is at least $10^{-7}$M, and more preferably, between about $10^{-8}$M and about $10^{-11}$M.

When binding specificity is achieved by base pairing, such pairing may be WatsonCrick pairing and/or Hoogsteen pairing. Preferably, binding specificity in the case of polynucleotide targets is achieved by a combination of both Watson-Crick and Hoogsteen pairing by the use of an oligonucleotide clamp.

The oligonucleotide moieties of the branched polymers may be synthesized by conventional means on a commercially available automated DNA synthesizer, e.g. an Applied Biosystems (Foster City, Calif.) model 392 or 394 DNA/RNA synthesizer. Preferably, phosphoramidite chemistry is employed, e.g. as disclosed in the following references: Beaucage and Iyer, Tetrahedron, 48:2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. For some applications, nuclease resistant backbones may be preferred. Many types of modified oligonucleotides are available that confer nuclease resistance, e.g. phosphorothioate, phosphorodithioate, phosphoramidate, or the like, described in many references, e.g. phosphorothioates: Stec et al, U.S. Pat. No. 5,151,510; Hirschbein, U.S. Pat. No. 5, 166,387; Bergot, U.S. Pat. No. 5, 183,885; phosphoramidates: Froehler et al, International application PCT/US90/03138; and for a review of additional applicable chemistries: Uhlmann and Peyman (cited above).

In accordance with the invention, branched or multiply connected macromolecular structures comprise a plurality of polymeric units that comprise signal generation moieties. These moieties are molecular structures that directly or indirectly generate a signal, e.g. fluorescent, colorimetric, radioactive, or the like, that can be detected by conventional means. Direct signal generation means that the moiety producing a signal is covalently linked to the branched or multiply connected macromolecular structure, e.g. as with the covalent attachment of a fluorescent dye, enzyme, or the like. Indirect signal generation means that a structure is one component of a multi-component system that produces a signal, e.g. a polymeric unit comprising a biotin moiety for binding to a labeled avidin protein, an oligonucleotide moiety which anneals to a complementary oligonucleotide (which may be part of another branched or multiply connected macromolecular structure) that has a covalently attached fluorescent dye, or the like. Preferably, the signal generation moiety comprises a first oligonucleotides of about 12 to about 50 nucleotides in length. In one aspect of this preferred embodiment, a signal is generated indirectly by providing a second oligonucleotide which is complementary to the first oligonucleotide and which has a fluorescent dye covalently attached. Attaching fluorescent dyes to oligonucleotides is well known in the art, e.g. U.S. Pat. Nos. 4,997,828; 5,151,507; 4,855,225; 5,188,934; Eckstein, editor (cited above); and the like. The number of signal generation moieties attached to a branched or multiply connected macromolecular structure depends on several factors, including the nature of the signal generated, the nature of the sample containing the target molecule, and the like. Preferably, a branched or multiply connected macromolecular structure employed as a probe comprises from 2 to about 15–20 signal generation moieties. More preferably, it comprises from 2 to about 10 signal generation moieties.

Convergent Assembly

Polymeric units are assembled by forming one or more covalent bridges among them.

Preferably, the bridges are formed by reacting thiol, phosphorothioate, or phosphorodithioate groups on one or more components with haloacyl- or haloalkylamimo groups on one or more other components to form one or more thio- or dithiophosphorylacyl or thio- or dithiophosphorylalkyi bridges. Generally, such bridges have one of the following forms:

$$\ldots -NHRSP(=Z)(O^-)O-\ldots$$

OR $$\ldots -NHRS-\ldots$$

wherein R is alkyl or acyl and Z is sulfur or oxygen. The assembly reaction may involve from 2 to 20 components depending on the particular embodiment; but preferably, it involves from 2 to 8 components; and more preferably, it involves from 2 to 4 components. Preferably, the haloacyl. or haloalkylamino groups are haloacetylamino groups; and more preferably, the haloacetylamino groups are bromoacetylamino groups. The acyl or alkyl moieties of the haloacyl- or haloalkylamino groups contain from 1 to 12 carbon atoms; and more preferably, such moieties contain from 1 to 8 carbon atoms. The reaction may take place in a wide range of solvent systems; but generally, the assembly reaction takes place under liquid aqueous conditions or in a frozen state in ice, e.g. obtained by lowering the temperature of a liquid aqueous reaction mixture. Alternatively, formation of thiophosphorylacetylamino bridges in DMSO/H2O has been reported by Thuong et al, Tetrahedron Letters, 28:4157–4160 (1987); and Francois et al, Proc. Natl. Acad. Sci., 86:9702–9706 (1989). Typical aqueous conditons include 4 μM of reactants in 25 mM NaCl and 15 mM phosphate buffer (pH 7.0).

The thio- or dithiophosphorylacyl- or thio- or dithiophosphorylalkylamino bridges are preferred because they can be readily and selectively cleaved by oxidizing agents, such as silver nitrate, potassium iodide, and the like. Preferably, the bridges are cleaved with potassium iodide, $KI_3$, at a concentration equivalent to about a hundred molar excess of the bridges. Usually, a $KI_3$ is employed at a concentration of about 0.1M. The facile cleavage of these bridges is a great advantage in synthesis of complex macromolecular structures, as it provides a convenient method for analyzing final products and for confirming that the structure of the final product is correct.

A 3'-haloacyl- or haloalkylamino (in this example, haloacetylamino) dervatized oligonucleotide 1 is reacted with a 5'-phosphorothioate derivatized oligonucleotide 2 according to the following scheme:

5'-N₁N₂N₃...N$_j$(3')—NHC(=O)CH₂X +
    1

S⁻P(=O)(O⁻)O—N₁N₂N₃...N$_k$-3' ⟶
    2

N₁N₂N₃...N$_j$—NHC(=O)CH₂SP(=O)(O⁻)O—N₁N₂N₃...N$_k$ wherein X is halo and $N_1, N_2, \ldots N_j$ and $N_k$ are nucleotides of a j-mer and k-mer, respectively. It is understood that the nucleotides are merely exemplary of the more general polymeric units, $(M-L)_n$ described above. Compound 1 can be prepared by reacting N-succinimidyl haloacetate in N,N-dimethylformamide (DMF) with a 3'-aminodeoxyribonucleotide precursor in a sodium borate buffer at room temperature. After about 35 minutes the mixture is diluted (e.g. with H₂O), desalted and, purified, e.g. by reverse phase HPLC. The Y-aminodeoxyribonucleotide precursor can be prepared as described in Gryaznov and Letsinger, Nucleic Acids Research, 20:3403–3409 (1992). Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropylethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18–20 hours at room temperature.

5' monophosphorothioate oligonucleotide 2 is formed as follows: A 5' monophosphate is attached to the 5' end of an oligonucleotide either chemically or enzymatically with a kinase, e.g. Sambrook et al, Molecular Cloning: A Laboratory Manual, 2nd Edition (Cold Spring Harbor Laboratory, New York, 1989). Preferably, as a final step in oligonucleotide synthesis, a monophosphate is added by chemical phosphorylation as described by Thuong and Asscline, Chapter 12 in, Eckstein, editor, Oligonucleotides and Analogues (IRL Press, Oxford, 1991) or by Horn and Urdea, Tetrahedron Lett., 27:4705 (1986) (e.g. using commercially available reagents such as 5' Phosphate-ON™ from Clontech Laboratories (Palo Alto, Calif.)). The 5'-monophosphate is then sulfufized using conventional sulfurizing agents, e.g. treatment with a 5% solution of S₈ in pyfidine/CS₂ (1:1, v/v, 45 minutes at room temperature); or treatment with sulfurizing agent described in U.S. Pat. Nos. 5,003,097; 5,151,510; or 5,166,387. Monophosphorodithioates are prepared by analogous procedures, e.g. Froehler et al, European patent publication 0 360 609 A2; Caruthers et al, International application PCT/US89/02293; and the like.

Likewise to the above, a 5'-haloacetylamino dervatized oligonucleotide 3 is reacted with a 3'-monophosphorothioate oligonucleotide 4 according to the following scheme:

3'-N₁N₂N₃...N$_j$(5')—NHC(=O)CH₂X +
    3

S⁻P(=O)(O⁻)O—(3')N₁N₂N₃...N$_k$-5' ⟶
    4

3'-N₁N₂N₃...N$_j$—NHC(=O)CH₂SP(=O)(O⁻)O—N₁N₂N₃...N$_k$-5' wherein the symbols are defined the same as above, except that the nucleotides monomers of the j- and k-mers are in opposite orientations. In this case, Compound 3 can be prepared by reacting N-succinimidyl haloacetate in N,N-dimethylformamide (DMF) with a 5'-aminodeoxyribonucleotide precursor in a sodium borate buffer at room temperature, as described above for the 3'-amino oligonucleotide. 5'-aminodeoxynucleosides are prepared in accordance with Glinski et al, J. Chem. Soc. Chem. Comm., 915–916 (1970); Miller et al, J. Org. Chem. 29:1772 (1964); Ozols et al, Synthesis, 7:557–559 (1980); and Azhayev et al, Nucleic Acids Research, 6:625–643 (1979); which are incorporated by reference.

The 3'-monophosphorothioate oligonucleotide 4 can be prepared as described by Thuong and Asscline (cited above). Oligonucleotides 1 and 4 and 2 and 3 may be reacted to form polymeric units having either two 5' termini or two 3' termini, respectively.

Reactive functionalities for the attachment of branches may be introduced at a variety of sites. Preferably, amino functionalities are introduce on a polymeric unit or loop at selected monomers or linking moieties which are then converted to haloacetylamino groups as described above. Amino-derivatized bases of nucleoside monomers may be introduced as taught by Urdea et al, U.S. Pat. No. 5,093,232; Ruth U.S. Pat. No. 4,948,882; Haralambidis et al, Nucleic Acids Research, 15:4857–4876 (1987); or the like. Amino functionalities may also be introduced by a protected hydroxyamine phosphoramidite commercially available from Clontech Laboratories (Palo Alto, Calif.) as Amino-modifier II™. Preferably, amino functionalities are introduced by generating a derivatized phosphoramidate linkage by oxidation of a phosphite linkage with I₂ and an alkyldiamine, e.g. as taught by Agrawal et al, Nucleic Acids Research, 18:5419–5423 (1990); and Jager et al, Biochemistry, 27:7237–7246 (1988).

Generally, for the above procedures, it is preferable that the haloacyl- or haloalkylamino derivatized polymeric units be prepared separately from the phosphorothioate derivatized polymeric units, otherwise the phosphorothioate moieties require protective groups.

Macrocycles, or polymeric loops, may be synthesized by several approaches, e.g. as described by Prakash and Kool, J. Am Chem. Soc., 114:3523–3527 (1992); Rumney and Kool, Angew. Chem. Int. Ed Engl., 31:1617 (1992); or the like. Briefly, in accordance with these methods, a linear polymeric unit is synthesized as described above after which a 5' terminal hydroxyl is phosphorylated. The linear polymer is then combined with a complementary template the brings the 3' and 5' ends of the linear polymer into juxtaposition where they are ligated using aqueous cyanogen bromide/imidazole/Ni²⁺. Such ligation can also be accomplished enzymatically under conventional conditions for commercially available ligases.

In one aspect of the invention, polymeric loops are assembled from two or more linear polymeric units separately prepared and derivatized exclusively with either phosphorothioate functionalities or with haloacyl- or haloalkylamino functionalities, as illustrated below:

XCH₂C(=O)NH-(5')N₁N₂N₃...N$_j$(3')-NHC(=O)CH₂X    5

SP(O=)(O⁻)O-(3')N₁N₂N₃...N$_k$(5')-OP(=O)(O⁻)S    6 where X, $N_1$, $N_2$, and the like, are defined above. Polymeric units 5 and 6 are assembled by combining them in solution followed by freezing, if the relative orientations of the units were not important, or by combining them with one or more templates to bring the appropriate termini into juxtaposition for ligation. Clearly, the latter approach, as with those described above, require that the polymeric loops contain oligonucleotide moieties for the template to function. Preferably, the template strand has a length of between about 12 to about 20–40 nucleotides.

Oligonucleotide Clamps

Preferably, the target binding moiety of a branched polymer is an oligonucleotide clamp, which is a compound capable of forming a covalently closed macrocycle or a stable circular complex after specifically binding to a target polynucleotide. Generally, oligonucleotide clamps comprise one or more oligonucleotide moieties capable of specifically binding to a target polynudeotide and one or more pairs of binding moieties eovalently linked to the oligonucleotide moieties. Upon annealing of the oligonucleotide moieties to the target polynucleotide, the binding moieties of a pair are brought into juxtaposition so that they form a stable covalent or non-covalent linkage or complex. The interaction of the binding moieties of the one or more pairs effectively clamps the specifically annealed oligonucleotide moieties to the target polynucleotide.

In one preferred form oligonucleotide clamps-comprise a first binding moiety, a first oligonucleotide moiety, a hinge region, a second oligonucleotide moiety, and a second binding moiety, for example, as represented by the particular embodiment of the following formula:

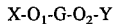

wherein $O_1$ and $O_2$ are the first and second oligonucleotide moieties, G is the hinge region, X is the first binding moiety and Y is the second binding moiety such that X and Y form a stable covalent or non-covalent linkage or complex whenever they are brought into juxtapositon by the annealing of the oligonucleotide moieties to a target polynucleotide, as illustrated diagrammatically in FIG. 1a. Preferably, in this embodiment, one of $O_1$ and $O_2$ undergoes Watson-Crick binding with the target polynucleotide while the other of $O_1$ and $O_2$ undergoes Hoogsteen binding.

Figure 1B:
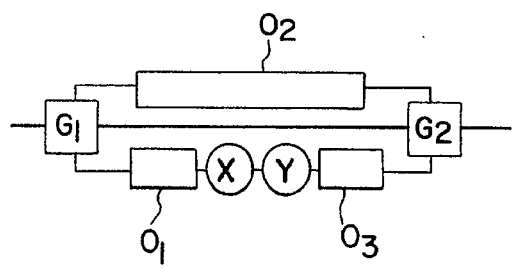

In another preferred form, oligonucleotide clamps comprise a first binding moiety, a first, second, and third oligonucleotide moiety, a first and second hinge region, and a second binding moiety, for example, as represented by the particular embodiment of the following formula:

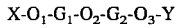

wherein X and Y are described as above, $G_1$ and $G_2$ are the first and second hinge regions, and $O_1$, $O_2$, and $O_3$ are the first through third oligonucleotide moieties. Preferably, the sequences of $O_1$, $O_2$, and $O_3$ are selected so that $O_1$ and $O_2$ and $O_3$ and $O_2$ form triplex structures with the target polynucleotide, as diagrammatically illustrated in FIG. 1b.

In embodiments where triplex formation is desired, there are constraints on the selection of target sequences. Generally, third strand association via Hoogsteen type of binding is most stable along homopyrimidine-homopurine tracks in a double stranded target. Usually, base triplets form in T-A*T or C-G*C motifs (where "–" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88:9397–9401 (1991); Roberts et al, Science, 258:1463–1466 (1992); Distefano et al, Proc. Natl. Acad. Sci., 90:1179–1183 (1993); Mergny et al, Biochemistry, 30:9791–9798 (1991); Cheng et al, J. Am. Chem. Soc., 114:4465–4474 (1992); Beal and Dervan, Nucleic Acids Research, 20:2773–2776 (1992); Beal and Dervan, J. Am. Chem. Soc., 114: 4976–4982 (1992); Giovannangeli et al, Proc. Natl. Acad. Sci., 89:863 1–8635 (1992); Moser and Dervan, Science, 238:645–650 (1987); McShan et al, J. Biol. Chem., 267:5712–5721 (1992); Yoon et al, Proc. Natl. Acad. Sci., 89:3840–3844 (1992); Blume et al, Nucleic Acids Research, 20:1777–1784 (1992); and the like. Generally, after one of the oligonucleotide moieties forms a Watson-Crick duplex with a pyrimidine-rich or purine-rich track in a target polynucleotide, the remaining oligonucleotide components bind to the major groove of the duplex to form a triplex structure.

Selection of particular oligonucleotide sequences for triplex formation can also be carried out empirically, for example, through aptamer screening, or like process, where candidate oligonucleotide moieties are selected on the basis of binding strength to an immobilized double stranded target, e.g. Ellington and Szostak, Nature, 346:818–822 (1990); Toole et al, International application PCT/US92/01383; and the like.

Target polynucleotides may be single stranded or double stranded DNA or RNA; however, single stranded DNA or RNA target polynucleotides are preferred.

Preferably, stability of oligonucleotide clamp/target polynucleotide complexes are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and clamp concentrations at between about 1.0–2.0 μM. Typical conditions are as follows: 150 mM NaCl and 10 mM $MgCl_2$ in a 10 mM sodium phosphate buffer (pH 7.0) or in a 10 mM.Tris-HCl buffer (pH 7.0); or like conditions. Data for melting curves are accumulated by heating a sample of the oligonucleotide clamp/target polynucleotide complex from room temperature to about 85°–90° C. As the temperature of the sample increases, absorbance of 260 nm light is monitored at 1° C. intervals, e.g. using a Cary (Australia) model 1E or a Hewlett-Packard (Palo Alto, Calif.) model HP 8459 UV/VIS spectrophotometer and model HP 89100A temperature controller, or like instruments.

The length of the oligonucleotide moieties is sufficiently large to ensure that specific binding will take place only at the desired target polynucleotide and not at other fortuitous sites. The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, and the like. Preferably, the oligonucleotide moieties have lengths in the range of about 6 to 40 nucleotides. More preferably, the oligonucleotide moieties have lengths in the range of about 12 to 25 nucleotides.

Hinge regions consist of nucleosidic or non-nucleosidic polymers which preferably facilitate the specific binding of the monomers of the oligonucleotide moieties with their complementary nucleotides of the target polynucleotide. Generally, the oligonucleotide moieties may be connected to hinge regions and/or binding moieties in either 5'–>3' or 3'–>5' orientations. For example, in the embodiment described above comprising a first binding moiety, a first oligonucleotide moiety, a hinge region, a second oligonucleotide moiety, and a second binding moiety, the oligonucleotide moieties may have any of the following orientations:

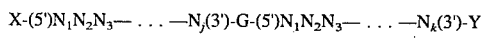

OR

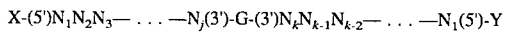

OR

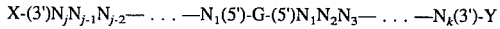

OR

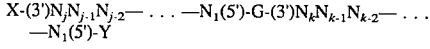

wherein $N_1N_2N_3— \ldots —N_k$ and $N_1N_2N_3- \ldots -N_j$ are k-mer and j-mer oligonucleotide moieties in the indicated orientations.

Preferably, the hinge region has the general form of the linear polymeric unit described above, with the following exceptions: n will vary from 1, for M comprising alkyl, alkenyl, and/or ethers containing 10 or more carbon atoms, e.g. Salunkhe et al, J. Am. Chem. Soc., 114:8768–8772 (1992), to about 10 for M comprising alkyl, alkenyl, and/or ethers containing 2–3 carbon atoms. Preferably, for a hinge moiety consisting entirely of an alkyl chain (and linkage moiety), such alkyl chain contains form 8 to 15 carbon atoms, and more preferably, from 9 to 12 carbon atoms. Preferably, for nucleoside-sized monomers, n varies between about 3 and about 10; and more preferably, n varies between about 4 and 8.

A variety of binding moieties are suitable for use with the invention. Generally, they are employed in pairs, which for convenience here will be referred to as X and Y. X and Y may be the same or different. Whenever the interaction of X and Y is based on the formation of stable hydrophobic complex, X and Y are lipophilic groups, including alkyl groups, fatty acids, fatty alcohols, steroids, waxes, fat-soluble vitamins, and the like. Further exemplary lipophilic binding moieties include glycerides, glyceryl ethers, phospholipids, sphingolipids, terpenes, and the like. In such embodiments, X and Y are preferably selected from the group of steroids consisting of a derivatized perhydrocyclopentanophenanthrene nucleus having from 19 to 30 carbon atoms, and 0 to 6 oxygen atoms; alkyl having from 6 to 16 carbon atoms; vitamin E; and glyceride having 20 to 40 carbon atoms. Preferably, a perhydrocyclopentanophenanthrene-based moiety is attached through the hydroxyl group, either as an ether or an ester, at its C3 position. It is understood tha X and Y may include a linkage group connecting it to an oligonucleotide moiety. For example, glyceride includes phosphoglyceride, e.g. as described by MacKellar et al, Nucleic Acids Research, 20:3411–3417 (1992), and so on. It is especially preferred that lipophilic moieties, such as perhydrocyclopentanophenanthrene derivatives, be linked to the 5' carbon and/or the 3' carbon of an oligonucleotide moiety by a short but flexible linker that permits the lipophilic moiety to interact with the bases of the oligonucleotide clamp/target polynucleotide complex or a lipophilic moiety on the same or another oligonucleotide moiety. Such linkers include phosphate (i.e. phosphodiester), phosphoramidate, hydroxyurethane, carboxyaminoalkyl and carboxyaminoalkylphosphate linkers, or the like. Preferably, such linkers have no more than from 2 to 8 carbon atoms.

Binding moieties can be attached to the oligonucleotide moiety by a number of available chemistries. Generally, it is preferred that the oligonucleotide be initially derivatized at its 3' and/or 5' terminus with a reactive functionality, such as an amino, phosphate, thiophosphate, or thiol group. After derivatization, a hydrophilic or hydrophobic moiety is coupled to the oligonucleotide via the reactive functionality. Exemplary means for attaching 3' or 5' reactive functionalities to oligonucleotides are disclosed in Fung et al, U.S. Pat. No. 5,212,304; Connolly, Nucleic Acids Research, 13:4485–4502 (1985); Tino, International application PCT/US91/09657; Nelson et al, Nucleic Acids Research, 17:7187–7194 (1989); Stabinsky, U.S. Pat. No. 4,739,044; Gupta et al, Nucleic Acids Research, 19:3019 (1991); Reed et al, International application PCT/US91/06143; Zuckerman et al, Nucleic Acids Research, 15:5305 (1987); Eckstein, editor, Oligonucleotides and Analogues: A Practical Approach (IRL Press, Oxford, 1991); Clontech 1992/1993 Catalog (Clontech Laboratories, Palo Alto, Calif.); and like references.

Preferably, whenever X and Y form a covalent linkage, X and Y pairs must react specifically with each other when brought into juxtaposition, but otherwise they must be substantially unreactive with chemical groups present in a cellular environment. In this aspect of the invention, X and Y pairs are preferably selected from the following group: when one of X or Y is phosphorothioate or phosphorodithioate, the other is haloacetyl, haloacyl, haloalkyl, or alkylazide; when one of X or Y is thiol, the other is alkyl iodide, haloacyl, or haloacetyl; when one of Y or Y is phenylazide the other is phenylazide. More preferably, when one of X or Y is phosphorothioate or phosphorodithioate, the other is haloacetyl, haloacyl, or haloalkyl, wherein said alkyl, acetyl, or acyl moiety contains from one to eight carbon atoms.

In some embodiments, X and Y may form a covalent linkage in the presence of an activating agent. That is, one or both of the binding moieties are activated or rendered reactive towards one another by exposure to an activating agent or condensing agent, such as radiation, a reducing agent, an oxidizing agent, or the like. Exemplary, binding moieties employing activating agents include thiophosphoryl groups in the presence of $K_3Fe(CN)_6$ or $KI_3$, e.g. Gryaznov and Letsinger, Nucleic Acids Research, 21:1403–1408 (1993); phosphoryl and hydroxyl in the presence of N-cyanoimidazole, e.g. Luebke et al, J. Am. Chem. Soc., 113:7447–7448 (1991); phosphoryl or amino group and hydroxyl in the presence of cyanogen bromide, e.g. Sokolova et al, FEBS Letters, 232:153–155 (1988); phosphoryl and hydroxyl groups in the presence of spermine-5-(N-ethylimidazole)carboxamide and cyanoimidazole, e.g. Zuber et al, J. Am. Chem. Soc., 115:4939–4940 (1993); and the like.

Polynucleotide Detection Assays

Branched polymers of the invention are employed as diagnostic probes to detect the presence of one or more target molecules, especially target polynucleotides, in a wide range of samples, including environmental samples, e.g. from public water supplies, samples from foodstuffs, and from other biological samples, such as blood, saliva, semen, amniotic fluid, tissue homogenates of plants or animals, or of human patients, and the like. The use of nucleic acid probes in human diagnostics, forensics, and genetic analysis has been extensively reviewed. For example, the following references describe many diagnostic applications of nucleic acid probes for which the present invention can be usefully employed: Caskey, Science 236:1223–1228 (1987); Landegren et al, Science, 242:229–237 (1988); and Arnheim et al, Ann. Rev. Biochem, 61:131–156 (1992). Moreover, there is extensive guidance in the literature concerning the selection of hybridization conditions, labeling means, and the like, which is applicable to the practice of the present invention, e.g. Wallace et al, Nucleic Acids Research 6:3543–3557 (1979); Crothers et al, J. Mol. Biol. 9:1–9 (1964); Gotoh, Adv. Biophys. 16:1–52 (1983); Wetmer, Critical Reviews in Biochemistry and Molecular Biology 26:227–259 (1991); Breslauer et al, Proc. Natl. Acad. Sci. 83: 3746–3750 (1986); Wolf et al, Nucleic Acids Research, 15:2911–2926 (1987); McGraw et al, Biotechniques, 8:674–678 (1990), and the like.

Branched polymers of the invention may be used in essentially any of the known solution or solid phase hybridization formats, such as those in which the analyte is bound directly to a solid phase, or sandwich hybridizations in which the analyte is bound to an oligonucleotide that is, in turn, bound to a solid phase. Oligonucleotide clamps having an oligonucleotide "tail" attached to a hinge region are particularly useful in conjunction with branched polymer amplification schemes, such as those of the present invention and those disclosed by Urdea et al, U.S. Pat. No. 5,124,246; Wang et al, U.S. Pat. No. 4,925,785; and the like. Urdea et al and Wang et al are incorporated by reference for their description of such hybridization assays. In such embodiments, the oligonucleotide clamp serves as a highly stable "capture" probe by binding to a target polynucleotide analyte of interest. The oligonucleotide tail then hybridizes with a directly or indirectly labeled amplifier strand or complex. Such tails are long enough to form a stable duplex with the amplifier strand. Preferably, such tails are between 18 and 60 nucleotides in length.

Oligonucleotide tails may be coupled to hinge regions at a phosphoramidate linkage or an amino derivatized monomer, such as aminomodifier II™, available from Clontech Laboratories (Palo Alto, Calif.). As described above for polymeric units, the amino group may be converted to a haloacetylamino, or like group, then reacted with an oligonucleotide having either a 5' or 3' phosphorothioate or phosphorodithioate group to form a thiophosphorylacetylamino, or like, bridge, as described above.

Generally, use of the branched or multiply connected macromolecular structures of the invention as molecular probes comprises (i) contacting the compound(s) with a sample in a complexing buffer, described more fully below, (ii) separating specifically bound compound from nonspecifically bound or excess compound, and (iii) detecting a signal generated directly or indirectly by the specifically bound compound. These steps are well known in art, but require routine optimization of such parameters as salt concentration, temperature, blocking agents, and the like, for particular embodiments. Preferably, whenever the target molecule is a polynucleotide and specific binding is achieved by Watson-Crick type and/or Hoogsteen type base pairing, the concentration of the branched or multiply connected macromolecular structure of the invention is in about 10- to 100-fold molar excess of the target polynucleotide.

Kits incorporating branched polymers of the invention can take a variety of forms depending on the particular embodiment, the type of assay format employed, and the labeling scheme employed. In one aspect, kits of the invention comprise a branched polymer specific for a given target molecule, a complexing buffer, and a labeling means. As used herein, "complexing buffer" means as solvent system, usually aqueous, that permits specific binding of the target binding moiety to its target molecule. The composition of the complexing buffer depends on the type of target molecule and on the nature of the sample in which the assay is carded out, e.g. to what extent there may be interfering molecular species. For protein targets, the complexing buffer is a mild saline solution, e.g. between about 10 to 500 mM NaCl or its equivalent in a neutral buffer, e.g. 50 mM Tris-HCl (pH 7–8). The following references provide guidance for selecting appropriate conditions: Kinzler et al, Nucleic Acids Research, 17:3645–3653 (1989); Thiesen et al, Nucleic Acids Research, 18:3203–3209 (1990); Oliphant et al, Mol. Cell. Biol., 9:2944–2949 (1989); and the like. The complexing buffer may contain additional components such as detergents, surfactants, chelating agents, carder compounds, e.g. bovine serum albumin, blocking agents, as described below, and the like.

For polynucleotide targets, the complexing buffer is a hybridization buffer. That is, it is a saline solution of about 100 mM to about 1M NaCl, of its equivalent, generally buffered at neutral pH, e.g. pH 7–8. A with complexing buffers, a hybridization buffer may contain additional components such as detergents, surfactants, chelating agents, carrier compounds, e.g. bovine serum albumin, blocking agents, as described below, and the like.

In yet another aspect, kits of the invention comprise an oligonucleotide clamp specific for a given target polynucleotide, a branched polymer operationally associated with the oligonucleotide clamp; a hybridization buffer, and a labeling means. As used herein, "operationally associated with" means an oligonucleotide clamp is covalently attached to the branched polymer, or is capable of binding or complexing specifically with the branched polymer, e.g. in the case of a oligonucleotide clamp dimer wherein one of the clamps is specific for a sequence of the branched polymer. Kits of the invention may further comprise wash buffers for removing unbound label and/or oligonucleotide clamps, solid phase supports such as derivatized magnetic beads, or the like; and prehybridization buffers containing blocking agents, e.g. Denhardt's solution, sonicated salmon sperm DNA, detergents such as 1% SDS, or the like, for minimizing nonspecific binding of oligonucleotide clamps or other nucleosidic binding components, such as amplifier strands. An exemplary hybridization buffer comprises the following reagents: 100 mM NaCl, 10 mM $MgCl_2$, and 10 mM Tris-HCl (pH 7.0).

EXAMPLE 1

Synthesis of Oligonucleotide Clamp having 3' and 5' Cholesterol Binding Moieties for pol and nef genes of HIV The series of oligonucleotide clamps listed in Table I were synthesized that have cholesterol moieties attached to either a 5' end, a 3' end, or to both a 3' end and a 5' end. The 3' cholesterol was attached by first constructing a cholesterol-derivatized solid phase support followed by routine oligonucleotide chain extension via phosphoramidite monomers on a conventional automated DNA synthesizer (Applied Biosystems model 394). The 5' cholesterol was attached in the final coupling step of the synthesis by reacting cholesterol chloroformate with the terminal nucleotide having a 5' amino group or by coupling a cholesterol phosphoramidite with a terminal hydroxyl group, the former method usually giving higher yields. Such clamp are readily attached to other polymeric units by introducing a free amine group, e.g. via AminoModifier II (Clontech) during synthesis, followed by bromoacetylation, and coupling via a phosphorothioate group, as discussed above.

(1) A polymer supported oligonucleotide, 1 μmole scale, with terminal 5'-amino group was treated with 2 ml of a 10% solution of cholesteryl formate in chloroform/diisopropylethylamine (9:1, v:v) for 20 minutes at room temperature. The polymer support was then washed with chloroform and acetonitrile, cleaved and deprotected with concentrated ammonium (5 hours at 55° C.), and purified by reverse phase HPLC.

(2) A polymer supported oligonucleotide, 1 μmole scale, with terminal hydroxyl group was treated with 250 μl of 0.1M solution of cholesterol phosphoramidite in chloroform and 250 μl of 0.45M solution of tetrazole in acetonitrile for 10–15 minutes at room temperature. The polymer support was then washed with acetonitrile, cleaved and deprotected with concentrated ammonium (5 hours at 55° C.), and purified by reverse phase HPLC.

The oligonucleotides and oligonucleotide clamps listed in Table I were designed to specifically bind to the following single stranded or double stranded target polynucleotides (segment of the pol and nef genes of HIV) Seq ID No: 1:

```
5'---AAAAGAAAAGGGGGGA---3'
3'---TTTTCTTTTCCCCCCT---5'
      Double stranded DNA 5'---AAAAGAAAAGGGGGGA---3'
  Single stranded RNA or DNA
```

EXAMPLE 2

Synthesis of Oligonucleotide Clamp with Cholesterol Binding Moieties, a Polyethylene Glycol Hinge Region, and a Free Amine The following oligonucleotide clamp having a non-nucleosidic hinge region is synthesized as described above. In the hinge region, protected polyethyl glycol phosphoramidites disclosed by Durand et al, Nucleic Acids Research, 18:6353–6359 (1990); and Rumney et al (cited above) are employed along with AminoModifier II from Clontech (Palo Alto, Calif.):

5'-Chol-
CACTTTTCTTTTGGGGGGp(OCH$_2$CH$_2$)$_2$pCH$_2$CH(CH$_2$N H$_2$)p-(OCH$_2$CH$_2$)$_2$pTCCCCCCTTTTCTTTTCA-Chol-3' wherein "p" indicates the presence of a phosphodiester linkage, the nucleotide sequence to the left of the first "p" is SEQ ID NO:17 and the nucleotide sequence to the right of the fourth "p" is SEQ ID NO:18.

EXAMPLE 3

Synthesis of Oligonucleotide Clamp with Free Amine and Two Oligonucleotide Moieties in Opposite Orientations with respect to Hinge Region The following oligonucleotide clamps are prepared by the procedures described above and as noted below. the nucleotide sequence represented in a is SEQ ID NO:19 and the nucleotide sequence represented in b is SEQ ID NO:20.

5'-Chol- CACTGGGGGGTTTTGTTTTCA-(CH$_2$)$_6$NHC(=O)CH$_2$Br     a

5'-Chol-ACTCCCCCCTTTTCTTTTCApCH$_2$CH(CH$_2$NH$_2$)OP(=O)(O$^-$)S     b

5'-Chol-CACTGGGGGGTTTTGTTTTCA(3')-X-(3')ACTT-
TTCTTTTCCCCCCTCA-Chol-5'     c wherein X is —(CH$_2$)$_6$NHC(=O)CH$_2$SP(=O)(O$^-$)OCH(CH$_2$NH$_2$)CH$_2$OP(=O)(O$^-$)—.

Polymeric units a and b are separately synthesized and purified, after which they are combined in solution and frozen, as described above, to give oligonucleotide clamp c. 3'-bromoacetylamino-5'-Chol-oligonucleotides are prepared as follows: 15 μL of 0.4 M N-succinimidyl bromoacetate

TABLE I

| SEQ ID NO: | Designation | Sequence of Oligonucleotide Clamp* |
|---|---|---|
| 2 | 050A | 5'-CACTTTTC$^{Me}$TTTTCCCCCCTCACACTCCCCCCTTTTCTTTTAC-Chol |
| 2 | 050B | 5'-Chol-CACTTTTC$^{Me}$TTTTCCCCCCTCACACTCCCCCCTTTTCTTTTAC-Chol |
| 2 | 051 | 5'-Chol-CACTTTTC$^{Me}$TTTTC$^{Me}$C$^{Me}$C$^{Me}$C$^{Me}$C$^{Me}$C$^{Me}$TCACACTCCCCCCTTTTCTTTTAC-Chol |
| 2 | 052A | 5'-CACTTTTC$^{Me}$TTTTCCCCCCTCACACTC$^{Me}$C$^{Me}$C$^{Me}$C$^{Me}$C$^{Me}$C$^{Me}$TTTTCTTTTAC-Chol |
| 2 | 052B | 5'-Chol-CACTTTTC$^{Me}$TTTTCCCCCCTCACACTC$^{Me}$C$^{Me}$C$^{Me}$C$^{Me}$C$^{Me}$C$^{Me}$TTTTCTTTTAC-Chol |
| 3 | 053 | 5'-Chol-CACTTTTC$^{Me}$TTTTGGGGGGTCACACTCCCCCCTTTTCTTTTAC-Chol |
| 3 | DL015 | 5'-CACTTTTCTTTTGGGGGGTCACACTCCCCCCTTTTCTTTTAC |
| 3 | DL014 | 5'-CACTTTTCTTTTGGGGGGTCACACTCCCCCCTTTTCTTTTAC-Chol |
| 3 | DL013 | 5'-Chol-CACTTTTCTTTTGGGGGGTCACACTCCCCCCTTTTCTTTTAC-Chol |
| 4 | DL021 | 5'-Chol-TTTTCTTTTCACACTTTTCTTTTGGGGGGTCACACTCCCCCC-Chol |
| 13 | DL022 | 5'-Chol-CACTTTTCTTTTCCCCCCTCACACACTCCCCCCTTTTCTTTTAC-Chol |
| 14 | DL023 | 5'-Chol-TTTTCTTTTCACACTTTTCTTTTCCCCCCTCACTCCCCCC-Chol |

*"Chol" represents cholesterol and C$^{Me}$ represents 5-methylated cytidine.

The melting temperature of the following compounds were determined by computing the half maximum of the 260 nm absorption v. temperature curve, as described above: DL015: 39° C.; DL014: 58° C.; DL013: 68° C.; DL021: 67.5° C.; DL022: 67° C.; and control (two unconnected oligonucleotides withing binding moleties having sequences: 3'-TTTTCTTTTCCCCCCT-5' (SEQ ID NO: 16) and 5'-TTTTC$^{Me}$TTTT(C$^{Me}$)$_6$-3'(SEQ ID NO:15): 32° C.

(e.g. Calbiochem) in N,N-dimethylformamide (DMF) is added to 4.9 $A_{260}$ units of a 5'-Chol-3'-amino-oligonucleotide precursor in 10 mL of 0.2M sodium borate buffer at room temperature. After about 35 minutes the mixture is diluted (0.5 mL $H_2O$), desalter by gel filtration on a NAP-5 column (Pharmacia), purified by reverse phase I-IPLC (as described below), and again desalter to yield 4 $A_{260}$ units of 3'-bromoacetylamino-5'-Chol-oligonucleotide (elution time for reverse phase HPLC, 17.4 minutes; ion exchange HPLC, 17.4 minutes). Ion exchange HPLC is carried out on a Dionex Omni Pak NA100 4×250 mm column at pH 12 (0.001M NaOH) with a 2%/minute gradient of 1.0M NaCl in 0.01M NaOH. Reverse phase HPLC is carried out On a Hypersil ODS 4.6×200 mm column with a 1%/minute gradient of acetonitrile in 0.03M triethylammonium acetate buffer, pH 7.0. The 5'-Chol-3'-amino-oligonucleotide is prepared as described above. The 5'-Chol-3'-phosphorothioate oligonucleotide is prepared as described above.

EXAMPLE 4

Synthesis of Oligonucleotide Clamp Carrying a Oligonucleotide Attached to Hinge Region The oligonucleotide clamp of Example 2 is synthesized with the free primary amine in its hinge region. The amine is derivatized with bromoacetyl as described above. Separately, an oligonucleotide is prepared having either a 3' or 5' monophosphorothioate group, as desired. The bromoacetylated clamp and the oligonucleotide are combined in an aqueous solution and frozen as described above.

EXAMPLE 5

Synthesis of Oligonucleotide Clamp Dimer

The two oligonucleotide clamps shown below having free amines in their hinge regions are separately synthesized and bromoacetylated as described in Example 2. In a third synthesis, an oligonucleotide, or other linear polymeric unit, is prepared which has a monophosphorothioate group at both its 5' and 3' ends.

5'-Chol-CACTTTTC$^{Me}$TTTTCCCCCCTCAC(pnp)ACTCCCCCCTTTTCTTTTAC(3')-Chol    d

5'-Chol-TTTTTTTTTTTTCAC(pnp)ACTTTTTTTTTTTT(3')-Chol   e

SP(O$^-$)(=O)(CH$_2$)$_{2p}$(OCH$_2$CH$_2$p)$_{18}$(CH$_2$)$_2$OP(O$^-$)(=O)S    f wherein "pnp" represents a linkage or monomer containing an bromoacetylamino functionality and "p" is a phosphodiester linkage. The nucleotide sequence represented in d is SEQ ID NO:2, the nucleotide sequence between 5'-Chol and (pnp) in e is SEQ ID NO:5, and the nucleotide sequence between (pnp) and (3')-Chol in e is SEQ ID NO:6. After purification d, e, and f are combined in solution and frozen as described above. The oligonucleotide clamp dimer is then purified by gel electrophoresis.

EXAMPLE 6

Figure 2:
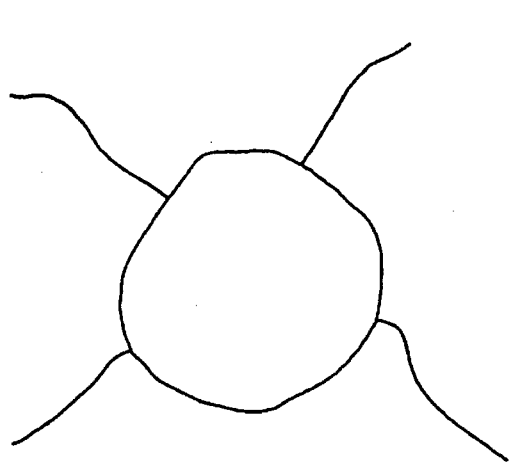

Synthesis of Loop Polymer having Four Branches and an Oligonucleotide Clamp Recognition Sequence The following oligonucleotides are synthesized as described below:

5'-BrCH$_2$C(=O)NHCACACA(pnp)CACACA(pnp)
CACAACACAC(pnp)ACACAC(pnp)ACACAC(3')
NGC(=O)CH$_2$Br    g 5'-SP(O$^-$)(=O)CAAAAAAAAAAAAACP(=O)(O$^-$)S    h 5'-SP(O$^-$)(=O)GGACCAATTTCCGGATTCTCGGGCAGAG-3'    i wherein the "pnp" is defined as above. The nucleotide sequence represented in g is SEQ ID NO:7, the nucleotide sequence represented in h is SEQ ID NO:8, and the nucleotide sequence represented in i is SEQ ID NO:9. The 12-mer poly-A segment in h is the oligonucleotide clamp recognition sequence. The bromoacetylamino functionalities are introduced into g as described above. g and h are ligated in solution using a template (5'-TGTGTGG-GAAAAAAAAAAAAGGTGTGT; SEQ ID NO:21, after which the resulting loop is purified by preparative gel electrophoresis. The purified loop is then mixed with i and frozen as described above and the product, illustrated in FIG. 2, is purified by gel electrophoresis.

EXAMPLE 7

Synthesis of Loop-and-branch Polymer Covalently Attached to Oligonucleotide Clamp The following oligonucleotides are synthesized in accordance with the procedures set forth above:

5'-Chol-TTTTTTTTTTTTCAC(pnp)ACTTTTTTTTTTTT(3')-Chol    j

5'-BrCH2C(=O)NH-CACACACACACACACACACACAC(pnp)ACACCACACACACACACAC(3')-NH-C(=O)CH$_2$Br    k 5'-SP(O$^-$)(=O)CACACACACACACACACACACACAC(3')OP(O$^-$)(=O)S    l wherein "(pnp)" is as described above. k and l are combined and circularized in solution with the help of a template as described above. The nucleotide sequence between 5'-Chol and (pnp) in j is SEQ ID NO:5, the nucleotide sequence between (pnp) and (3')-Chol in j is SEQ ID NO:6, the nucleotide sequence represented in k is SEQ ID NO:22 and the nucleotide sequence represented in l is SEQ ID NO:23. Purified k is then combined with j and l (which also serves as a tether) in solution then frozen as described above. The product is purified by conventional preparative gel electrophoresis. The "CA" repeats of k and l are readily substituted with recognition seqences for further oligonucleotide clamps.

EXAMPLE 8

Synthesis of Comb-Type Branched Polymer Having 3' Termini

The following oligonucleotides are synthesized in accordance with the procedures set forth above:

5'-SP(O$^-$)(=O)CACATAGGCATCTCCTAGTGCAGGAAGA-3'    m

3'-CA(pnp)CACACA(pnp)CACACA(pnp)CACACACA-(5')NH-C(=O)CH$_2$Br    n

Figure 3:
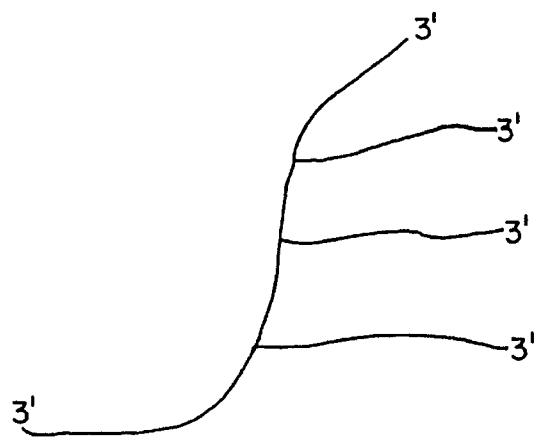
FIG. 3 diagrammatically illustrates the structure of a comb-type branched oligonucleotide polymer having three branches and only 3' termini.

5'-SP(O$^-$)(=O)CACA-CAAAAAAAAAAAAAAAAAAAAAAAA-3'    o wherein "pnp" is as described above. The nucleotide sequence represented in m is SEQ ID NO:10, the nucleotide sequence represented in n is SEQ ID NO:24, and the nucleotide sequence represented in o is SEQ ID NO:12, m and n combined in solution with a template (e.g. 5'-GTGTGT(3')NHC(=O)CH$_2$SP(=O)(O$^-$)(3')GTGTAT-5') as described above to form a 3'—3' polymeric unit containing three internal bromoacetylated amino groups. The 3'—3' polymeric unit is then combined with o in solution, after which the mixture is frozen as described above. The product, illustrated in FIG. 3, is purified by conventional gel electrophoresis.

EXAMPLE 9

Synthesis Of Comb-Type Branched Polymer Having 5' Termini

The following oligonucleotides are synthesized in accordance with the procedures set forth above:

5'-TAGGCATCTCCTAGTGCAGGAAGACACACA-(3')OP(O$^-$)(=O)S     p

5'-CA(pnp)CACACA(pnp)CACACA(pnp)CACA-CACACACAC-(3')NH-C(=O)CH$_2$Br     q

Figure 4:
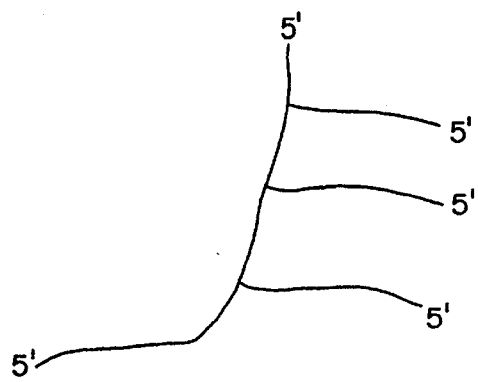
FIG. 4 diagrammatically illustrates the structure of a comb-type branched oligonucleotide polymer having three branches and only 5' termini.

5'-CACACAAAAAAAAAAAAAAAAAAAAAAAAAAA-(3')OP(O$^-$)(=O)S     r wherein "pnp" is as described above. The nucleotide sequence represented in p is SEQ ID NO:11, the nucleotide sequence represented in q is SEQ ID NO:25 and the nucleotide sequence represented in r is SEQ ID NO:12, p and q are combined in solution with a template as described above to form a 5=—5' polymeric unit containing three internal bromoacetylated amino groups. The 5'—5' polymeric unit is then combined with r in solution after which the mixture is frozen as described above. The product, illustrated in FIG. 4, is purified by conventional gel electrophoresis.

EXAMPLE 10

Synthesis of a Comb-Type Branched Polymer Without Template

The following oligonucleotides are synthesized in accordance with the procedures set forth above and purified by conventional methods. The nucleotide sequence represented in s, below is SEQ ID NO:26 and the nucleotide sequence represented in t, below, is SEQ ID NO:12.

Figure 5:
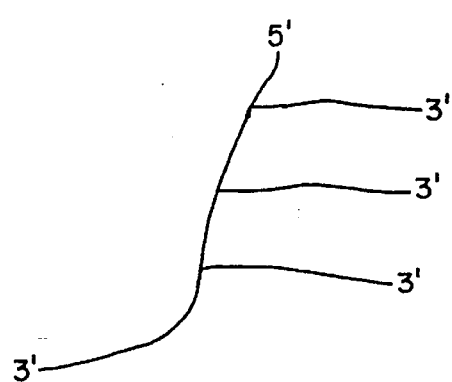
FIG. 5 diagrammatically illustrates the structure of a comb-type branched oligonucleotide polymer having both 3' and 5' termini.

5'-TAGGCATCTCCTAGTGCAGGAAGACACA-CA(pnp)CACACA(pnp)CACACA(pnp)CACACA(pnp)CA-3'     s 5'-SP(O$^-$)(=O)CACA-CAAAAAAAAAAAAAAAAAAAAAAAAAA-3'     t s and t are combined in solution and frozen as described above to form a 3'–5' comb-type branched polymer having four branches for annealing signal generating means. The product, illustrated in FIG. 5, is purified by conventional gel electrophoresis.

EXAMPLE 11

Synthesis Of a Comb-Type Branched Polymer With Biotinylated Branches

The following oligonucleotides are synthesized in accordance with the procedures set forth above and purified by conventional methods. Biotin was couple to v using a commercially available biotin phosphoramidite (Applied Biosystems, Inc., Foster City). The nucleotide sequence represented in u, below, is SEQ ID NO:26.

Figure 6:
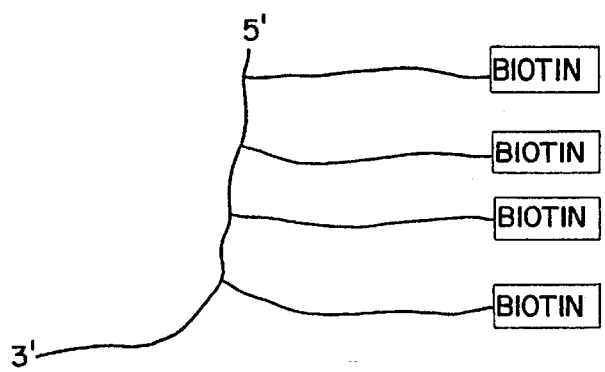
FIG. 6 diagrammatically illustrates the structure of a comb-type branched polymer having four biotins attached via polyethylene glycol linker arms.
Figure 7:
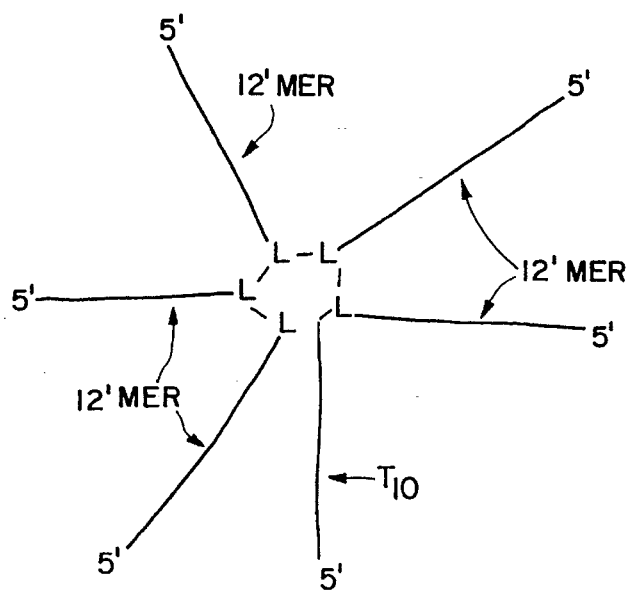

5-TAGGCATCTCCTAGTGCAGGAAGACACA-CA(pnp)CACACA(pnp)CACACA(pnp)CACACA(pnp)CA-3'     u 5'-biotin-OP(=O)(O$^-$)[OCH$_2$CH$_2$OP(=O)(O$^-$)]$_{12}$-OCH2CH2OP(O$^-$)(=O)S     v u and v are combined in solution and frozen as described above to form a 3'–5' comb-type branched polymer having four branches for annealing signal generating means. The product, illustrated in FIG. 6, is purified by conventional gel electrophoresis.

EXAMPLE 12

Synthesis of a Fork-Type Branched Polymer

The following oligonucleotides are synthesized in accordance with the procedures set forth above and purified by conventional methods. The nucleotide sequence represented in w, below, is SEQ ID NO:10 and the nucleotide sequence represented in x, below, is SEQ ID NO:12.

NH$_2$(CH$_2$)$_6$OP(=O)(O–)OCH(CH$_2$NH$_2$)OP(=O)(O–)-CACAT-AGGCATCTCCTAGTGCAGGAAGA-3'     w

5'-SP(O$^-$)(=O)CACA-CAAAAAAAAAAAAAAAAAAAAAAAAAA-3'     x

Terminal amine groups on polymeric unit w are attached by first coupling an AminoModifier II monomer to the 5' cytidine followed in the next synthesis cycle by coupling an AminoLinker II (CF$_3$C(=O)CH$_2$NH(CH2)$_6$-phosphoramidite) (available from Applied Biosystems, Inc., Foster City, Calif.) to the growing polymer. After cleavage and deprotection, the free amines are bromoacetylated as described above. The resulting product is purified and combined with x in aqueous solution and frozen, as described above, to yield the fork-type branched polymer.

---

I claim:

1. A branched or multiply connected macromolecular structure which specifically binds to a target molecule, the branched macromolecular structure comprising:

a plurality of covalently connected oligonucleotides, with at least one oligonucleotide comprising a target binding sequence that binds specifically and stably with a target molecule and at least two oligonucleotides comprising at least two signal generation moieties that directly or indirectly generate a signal, wherein said plurality of oligonucleotides are covalently connected by at least one branch point by one or more thiophosphorylalkylamino bridges formed from either a haloalkylamino derivatized oligonucleotide and a 5' phosphorothioate derivatized oligonucleotide or a haloalkylamino derivatized oligonucleotide and a 3' phosphorothioate derivatized oligonucleotide.

2. The branched or multiply connected macromolecular structure of claim 1 wherein said target binding sequence is an oligonucleotide clamp.

3. The branched or multiply connected macromolecular structure of claim 1 wherein said oligonucleotides are exclusively 3' termini or exclusively 5' termini.

4. A branched or multiply connected macromolecular structure of claim 1 wherein said thiophosphorylalkylamino bridge contains 1 to 12 carbon atoms.

5. A branched or multiply connected macromolecular structure of claim 4 wherein said plurality of oligonucleotides is less than 8 oligonucleotides.

6. A branched or multiply connected macromolecular structure of claim 1 having a comb structure.

7. A branched or multiply connected macromolecular structure of claim 1 wherein said target binding sequence ranges from 12 to 40 nucleotides in length.

8. A branched or multiply connected macromolecular structure of claim 1 wherein said target binding moiety has an affinity for a target of at least $10^{-7}$M.

9. A branched or multiply connected macromolecular structure of claim 1 wherein said signal generation moiety ranges from 12 to 50 nucleotides in length.

10. A branched or multiply connected macromolecular structure of claim 1 having a fork-like structure.

11. A branched or multiply connected macromolecular structure of claim 1 wherein there are 2 to 20 signal generation moieties.

12. A branched or multiply connected macromolecular structure of claim 1 wherein said signal generation moiety is selected from the group consisting of an oligonucleotide covalently linked to a fluorescent dye, oligonucleotide covalently linked to an enzyme, an oligonucleotide that anneals to a complementary oligonucleotide that is covalently attached to a fluorescent dye and an oligonucleotide that anneals to a complementary oligonucleotide that is covalently attached to a biotin molecule.

13. A branched or multiply connected macromolecular structure of claim 12 wherein there are 2 to 10 signal generation moieties.

14. A branched or multiply connected macromolecular structure of claim 1 wherein said signal generation moieties are oligonucleotide moieties that are covalently linked to said at least two oligonucleotides anneal to complementary oligonucleotides.

15. In a kit for detecting the presence of a target molecule in a sample, the kit of the type wherein a nucleic acid probe specific for the target molecule and a complexing buffer are provided, an improvement comprising:

a nucleic acid probe comprising a plurality of covalently connected oligonucleotides with at least one oligonucleotide comprising a target binding sequence that binds specifically and stably to with a target molecule and at least two oligonucleotides comprising at least two signal generation moieties that directly or indirectly generate a signal, wherein said plurality of oligonucleotides are covalently connected by at least one branch point with one or more thiophosphorylallcylamino bridges formed from either a haloalkylamino derivatized oligonucleotide and a 5' phosphorothioate derivatized oligonucleotide or a haloalkylamino derivatized oligonucleotide and a 3' phosphorothioate derivatized oligonucleotide.

16. The kit of claim 15 wherein said plurality of covalently connected oligonucleotides are defined by the formula:

$$(M-L)_n$$

wherein:

M is a nucleoside, or analog thereof;

L is a phosphorus (V) linking group; and n is in the range of from 3 to 100.

17. The kit of claim 16 wherein L is selected from the group consisting of phosphodiester, phosphotriester, methyl phosphonate, ethyl phosphonate, phosphorothioate, phosphorodithioate, and phosphoramidate.

18. The kit of claim 15 wherein said plurality of covalently connected oligonucleotides have one or more termini, wherein termini of said plurality are exclusively 3' termini or exclusively 5' termini.

19. The kit of claim 16 wherein said target molecule is a polynucleotide and said complexing buffer is a hybridization buffer.

20. A branched or multiply connected macromolecular structure of claim 19 wherein said signal generation moiety is selected from the group consisting of an oligonucleotide covalently linked to a fluorescent dye, oligonucleotide covalently linked to an enzyme, an oligonucleotide that anneals to a complementary oligonucleotide that is covalently attached to a fluorescent dye and an oligonucleotide that anneals to a complementary oligonucleotide that is covalently attached to a biotin molecule.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
    ( A ) LENGTH: 16 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:1:

AAAAGAAAAG GGGGGA 16

( 2 ) INFORMATION FOR SEQ ID NO:2:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:2:

CACTTTTCTT TTCCCCCTC ACACTCCCCC CTTTTCTTTT AC 42

( 2 ) INFORMATION FOR SEQ ID NO:3:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:3:

CACTTTTCTT TTGGGGGGTC ACACTCCCCC CTTTTCTTTT AC 42

( 2 ) INFORMATION FOR SEQ ID NO:4:

( i ) SEQUENCE CHARACTERISTICS:
    ( A ) LENGTH: 42 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:4:

TTTTCTTTTC ACACTTTTCT TTTGGGGGGT CACACTCCCC CC 42

( 2 ) INFORMATION FOR SEQ ID NO:5:

( i ) SEQUENCE CHARACTERISTICS:
    ( A ) LENGTH: 15 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:5:

TTTTTTTTTT TTCAC 15

( 2 ) INFORMATION FOR SEQ ID NO:6:

( i ) SEQUENCE CHARACTERISTICS:
    ( A ) LENGTH: 16 nucleotides
    ( B ) TYPE: nucleic acid
    ( C ) STRANDEDNESS: single
    ( D ) TOPOLOGY: linear (i i) MOLECULE TYPE: DNA (x i) SEQUENCE DESCRIPTION: SEQ ID NO:6:

ACTTTTTTTT TTTTTT 16

(2) INFORMATION FOR SEQ ID NO:7:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:7:

CACACACACA CACACACAAC ACACACACAC ACACAC 36

(2) INFORMATION FOR SEQ ID NO:8:

(i) SEQUENCE CHARACTERISTICS:
        (A) LENGTH: 14 nucleotides
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:8:

CAAAAAAAAA AAAC 14

(2) INFORMATION FOR SEQ ID NO:9:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:9:

GGACCAATTT CCGGATTCTC GGGAGAG 27

(2) INFORMATION FOR SEQ ID NO:10:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:10:

CACATAGGCA TCTCCTAGTG CAGGAAGA 28

(2) INFORMATION FOR SEQ ID NO:11:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:11:

TAGGCATCTC CTAGTGCAGG AAGACACACA 30

( 2 ) INFORMATION FOR SEQ ID NO:12:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

CACACAAAAA AAAAAAAAA AAAAAAAAA 30

( 2 ) INFORMATION FOR SEQ ID NO:13:

( i ) SEQUENCE CHARACTERISTICS:
        ( A ) LENGTH: 44 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

CACTTTTCTT TTCCCCCCTC ACACACTCCC CCCTTTTCTT TTAC 44

( 2 ) INFORMATION FOR SEQ ID NO:14:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

TTTTCTTTTC ACACTTTTCT TTTCCCCCCT CACTCCCCCC 40

( 2 ) INFORMATION FOR SEQ ID NO:15:

( i ) SEQUENCE CHARACTERISTICS:
        ( A ) LENGTH: 15 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

TTTTCTTTTC CCCCC 15

( 2 ) INFORMATION FOR SEQ ID NO:16:

( i ) SEQUENCE CHARACTERISTICS:
        ( A ) LENGTH: 16 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

TTTTCTTTTC CCCCCT 16

( 2 ) INFORMATION FOR SEQ ID NO:17:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

CACTTTTCTT TTGGGGGG                                                                                   18

( 2 ) INFORMATION FOR SEQ ID NO:18:

( i ) SEQUENCE CHARACTERISTICS:
            ( A ) LENGTH: 18 nucleotides
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:18:

TCCCCCCTTT TCTTTTCA                                                                                   18

( 2 ) INFORMATION FOR SEQ ID NO:19:

( i ) SEQUENCE CHARACTERISTICS:
            ( A ) LENGTH: 21 nucleotides
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:19:

CACTGGGGGG TTTTGTTTTC A                                                                               21

( 2 ) INFORMATION FOR SEQ ID NO:20:

( i ) SEQUENCE CHARACTERISTICS:
            ( A ) LENGTH: 20 nucleotides
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:20:

ACTCCCCCCT TTTCTTTTCA                                                                                 20

( 2 ) INFORMATION FOR SEQ ID NO:21:

( i ) SEQUENCE CHARACTERISTICS:
            ( A ) LENGTH: 27 nucleotides
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:21:

TGTGTGGGAA AAAAAAAAA GGTGTGT                                                                          27

( 2 ) INFORMATION FOR SEQ ID NO:22:

( i ) SEQUENCE CHARACTERISTICS:
            ( A ) LENGTH: 42 nucleotides
            ( B ) TYPE: nucleic acid
            ( C ) STRANDEDNESS: single
            ( D ) TOPOLOGY: linear ( i i ) MOLECULE TYPE: DNA ( x i ) SEQUENCE DESCRIPTION: SEQ ID NO:22:

CACACACACA CACACACACA CACACACCAC ACACACACAC AC　　　　　　　　　　　　42

( 2 ) INFORMATION FOR SEQ ID NO:23:

( i ) SEQUENCE CHARACTERISTICS:
    ( A ) LENGTH: 27 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:23:

CACACACACA CACACACACA CACACAC　　　　　　　　　　　　27

( 2 ) INFORMATION FOR SEQ ID NO:24:

( i ) SEQUENCE CHARACTERISTICS:
    ( A ) LENGTH: 28 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:24:

CACATAGGCA TCTCCTAGTG CAGGAAGA　　　　　　　　　　　　28

( 2 ) INFORMATION FOR SEQ ID NO:25:

( i ) SEQUENCE CHARACTERISTICS:
    ( A ) LENGTH: 29 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:25:

CACACACACA CACACACACA CACACACAC　　　　　　　　　　　　29

( 2 ) INFORMATION FOR SEQ ID NO:26:

( i ) SEQUENCE CHARACTERISTICS:
    ( A ) LENGTH: 50 nucleotides
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:26:

TAGGCATCTC CTAGTGCAGG AAGACACACA CACACACACA CACACACACA　　　　　　　　　　　　50